US010969484B2

(12) United States Patent
Alameri et al.

(10) Patent No.: US 10,969,484 B2
(45) Date of Patent: Apr. 6, 2021

(54) BULLET DETECTION SYSTEM

(71) Applicant: United Arab Emirates University, Al Ain (AE)

(72) Inventors: Mohammed Abdulhakeem Alameri, Al Ain (AE); Abdulrahim Ahmed Mohammed, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 16/570,039

(22) Filed: Sep. 13, 2019

(65) Prior Publication Data

US 2020/0233078 A1 Jul. 23, 2020

Related U.S. Application Data

(60) Provisional application No. 62/793,940, filed on Jan. 18, 2019.

(51) Int. Cl.
| G01S 13/88 | (2006.01) |
| F41H 11/00 | (2006.01) |
| F41H 9/06 | (2006.01) |
| A61B 5/06 | (2006.01) |
| A61B 5/0205 | (2006.01) |
| A61B 5/05 | (2021.01) |
| G01S 19/13 | (2010.01) |
| A61B 5/024 | (2006.01) |

(Continued)

(52) U.S. Cl.
CPC ........ *G01S 13/886* (2013.01); *A61B 5/02055* (2013.01); *A61B 5/061* (2013.01); *F41H 9/06* (2013.01); *F41H 11/00* (2013.01); *A61B 5/024* (2013.01); *A61B 5/05* (2013.01); *G01S 19/13* (2013.01)

(58) Field of Classification Search
CPC ...... G01S 13/003; G01S 13/887; F41H 11/02; F41G 3/147
See application file for complete search history.

(56) References Cited

U.S. PATENT DOCUMENTS

| 4,636,796 A | * | 1/1987 | Imazeki | ............... G01S 3/14 342/417 |
| 5,008,678 A | * | 4/1991 | Herman | ................. G01S 13/87 342/158 |

(Continued)

FOREIGN PATENT DOCUMENTS

| FR | 3008300 A1 * | 1/2015 | ......... A61B 5/02055 |
| GB | 1586159 A * | 3/1981 | ............... G01S 3/04 |

(Continued)

*Primary Examiner* — Bernarr E Gregory
(74) *Attorney, Agent, or Firm* — Hayes Soloway PC

(57) ABSTRACT

A portable Doppler microwave radar defense system that saves lives in dangerous situations, and alerts a person from surrounded threats, exposes enemy location, and shows the health data and injured person's location to remote server at a base. The system lets the person know about the surrounded threats before it happens, as it will detect any bullets in the detection zone and alert the person immediately from the incoming bullet within a long range which will let the person have seconds to avoid the bullet and save his life and the location of the shooter will be exposed to the person. The detection system can also be deployed over an object such as a car, truck, battle tank, aircraft, jet, helicopter, spaceship, or a satellite.

20 Claims, 6 Drawing Sheets

(51) Int. Cl.

| | |
|---|---|
| *F41G 3/14* | (2006.01) |
| *H01Q 1/32* | (2006.01) |
| *H01Q 1/27* | (2006.01) |
| *G01S 13/42* | (2006.01) |
| *G01S 7/03* | (2006.01) |
| *G01S 13/933* | (2020.01) |
| *F41H 5/08* | (2006.01) |
| *F41H 5/007* | (2006.01) |
| *F41H 3/02* | (2006.01) |
| *F42B 12/48* | (2006.01) |
| *F41H 1/02* | (2006.01) |
| *G01S 13/00* | (2006.01) |

(56) References Cited

U.S. PATENT DOCUMENTS

| | | | | |
|---|---|---|---|---|
| 5,111,210 | A * | 5/1992 | Morse | G01S 13/937 342/455 |
| 6,211,808 | B1 * | 4/2001 | Rees | G01S 13/933 342/29 |
| 6,549,158 | B1 * | 4/2003 | Hanson | F41G 7/2206 342/13 |
| 6,561,074 | B1 * | 5/2003 | Engel | F41F 3/0406 89/1.818 |
| 6,563,450 | B1 * | 5/2003 | Wallace | F41G 7/2206 342/100 |
| 6,575,400 | B1 * | 6/2003 | Hopkins | F41G 7/2206 244/3.19 |
| 6,755,795 | B2 * | 6/2004 | Marmaropoulos | A61B 5/02055 128/897 |
| 6,965,312 | B2 * | 11/2005 | Lerg | G08B 1/08 340/539.13 |
| 7,952,513 | B2 * | 5/2011 | Tietjen | G01S 13/862 342/52 |
| 8,149,156 | B1 * | 4/2012 | Allred | G01S 13/88 342/52 |
| 8,416,123 | B1 * | 4/2013 | Mitchell | G01S 13/42 342/107 |
| 8,442,615 | B2 * | 5/2013 | David | A61B 5/02055 600/388 |
| 8,510,869 | B1 * | 8/2013 | McCrady | A42B 3/046 2/410 |
| 8,947,195 | B1 * | 2/2015 | Anvari | A42B 3/046 340/3.1 |
| 8,981,989 | B2 * | 3/2015 | Gould | G01S 13/583 342/113 |
| 9,170,070 | B2 * | 10/2015 | Sharpin | G06T 7/246 |
| 9,423,495 | B1 * | 8/2016 | Chang | G01S 13/0218 |
| 10,108,783 | B2 * | 10/2018 | Horseman | A61B 5/1038 |
| 10,324,179 | B2 * | 6/2019 | Ling | G01S 13/91 |
| 10,495,751 | B2 * | 12/2019 | Moreira Neto | G01S 13/904 |
| 10,551,483 | B2 * | 2/2020 | Wyatt | G01S 13/89 |
| 2003/0117309 | A1 * | 6/2003 | Pappert | F41G 5/08 342/13 |
| 2005/0012657 | A1 * | 1/2005 | Mohan | G01S 13/003 342/133 |
| 2007/0018884 | A1 * | 1/2007 | Adams | G01S 13/003 342/147 |
| 2008/0291075 | A1 * | 11/2008 | Rapanotti | G01S 13/862 342/20 |
| 2012/0139786 | A1 * | 6/2012 | Puzella | G01S 13/87 342/368 |
| 2012/0267472 | A1 * | 10/2012 | Pratzovnick | B64C 39/024 244/13 |
| 2013/0192451 | A1 * | 8/2013 | Scott | F41G 3/147 89/41.05 |
| 2015/0301169 | A1 * | 10/2015 | De Pasquale | G01S 13/86 342/146 |
| 2015/0345907 | A1 * | 12/2015 | Varga | F41G 3/147 89/41.05 |
| 2016/0038083 | A1 * | 2/2016 | Ding | A61B 5/1121 600/388 |
| 2016/0061949 | A1 * | 3/2016 | Mohamadi | G01S 13/86 342/21 |
| 2017/0328684 | A1 * | 11/2017 | Kolanek | F41H 11/02 |

FOREIGN PATENT DOCUMENTS

| | | | | |
|---|---|---|---|---|
| GB | | 2333198 A * | 7/1999 | G01S 13/003 |
| WO | WO90/13048 A1 * | | 11/1990 | G01S 13/003 |
| WO | WO03/034890 A2 * | | 5/2003 | A61B 5/02055 |
| WO | WO2011/080688 A2 * | | 7/2011 | G01S 13/887 |

\* cited by examiner

US 10,969,484 B2

BULLET DETECTION SYSTEM

CROSS-REFERENCE TO RELATED APPLICATIONS AND PRIORITY

This patent application claims priority from U.S. Provisional Patent Application No. 62/793,940 filed Jan. 18, 2019, which is herein incorporated by reference in its entirety.

FIELD OF THE INVENTION

The present invention relates to the defense technology. More specifically, the present invention relates to a portable bullet detection system that works by microwave radar saving lives in a battlefield.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

In a battle, military or defense situation, there are numerous casualties both direct and indirect. These deaths mainly result from extreme environmental conditions, battle injuries from arms and ammunitions, delay in locating injured soldiers owing to which proper medical treatment cannot be provided resulting in death, failure to monitor the position of soldiers or injured men and so on and so forth.

If these problems were adequately solved, many lives could be saved during hostile situations. By providing accurate information about location and the physiological status of each individual, as well as communications equipment to convey the information to remote locations, a system for monitoring personnel could save many lives. Such monitors could be extremely valuable for military and law enforcement personnel, such as the Special Armed Forces, e.g. Rangers, who commonly train under extreme weather conditions, and in other dangerous environments. By monitoring physiological variables, those overseeing exercises can monitor the soldier, etc., and withdraw him/her from the exercise if it appears that harm is likely. In addition there is also a need for a system that could monitor a bullet fired from a rival gun, allowing the soldier to dodge the bullet, resulting in him/her saving his/her life. Presently there are monitors available in the market being used in the field of athletics to monitor the vital signs of an athlete or a hospital patient. These monitors are placed in wristbands or belts, which may be quickly attached to and removed from the athlete or patient and monitor a single vital sign such as a heart rate or temperature. However, these monitors cannot be used in combat situations, as they may not accurately determine patients or casualties in need of immediate medical care or evaluation. Further, these monitors cannot also detect an incoming bullet to the soldiers' position.

SUMMARY OF THE INVENTION

Thus, there is an imminent need for a detection system, that saves soldiers' lives in battlefield, and has many features such as alerting solider from surrounding threatening situation such as detecting an incoming bullet to the person's position, expose enemy location, and show the full health data of the injured solider along with the location to military camp.

Therefore it is an object of the present invention to provide for a bullet detection system to be deployed on a person's body that can detect an incoming bullet from an enemy gun allowing the person in the target zone to move or dodge the said bullet, saving his life.

Another advantage of the detection system of the present invention is to also expose the enemy location based on determining the trajectory, the cross section and the speed of the incoming bullet.

Another advantage of the present invention is to provide the physiological health data of a person, by providing health sensors in the system that effectively monitors the person's health and in case of any abnormal situation notify a remote monitoring unit at the base camp. It is also an object of the present invention to identify the source and type of weapon from which the bullet is released, by analysing the speed and cross section of the bullet enabling the personnel at the military base to know the weapons used by the enemies in the battlefield, thereby preparing the person in understanding the defense systems used by the rivals.

The detection system is lightweight, portable and could be easily placed on the person's body by installing it in a vest or a jacket. Also the detection system has a GPS system to constantly monitor the location of the person in the target zone.

In one aspect, the present invention provides for a bullet detection system comprising an array of radar antennas and corresponding feedback units for being deployed over a person's body, a microcontroller in connection with the array of radar antennas and feedback units for transmitting and receiving microwave signals detected by the antennas, for processing the received microwave signals to determine arrival of a bullet and the associated target location zone on the person's body where the bullet is directed and to activate a specific feedback unit (among the feedback units) positioned in the target location zone determined.

Preferably the feedback unit comprises of a plurality of sound generators, vibrators, electrical shock generators.

The array of radar antennas are in proximity with the feedback units, such as each radar antenna has a corresponding feedback unit positioned in proximity thereof. The radar antennas detect the microwave signals received, send these to the microcontroller for processing and determination of a bullet directed in the direction of the person which would be detected promptly upon release of the bullet from a gun barrel, to determine the exact target location zone on the person's body where the bullet is directed preferably based on the specific radar antenna having detected the arrival of such a bullet based on data signal processing analysis (such as higher signal power), and triggering the feedback unit associated with that specific radar antenna to provide a sensation in the specific part the body of the person in the bullet target location zone.

In some embodiments, the detection system further comprises a global positioning system to detect the location of the person in the target zone and transmit the same to a remote monitoring unit at a base camp.

The remote monitoring unit comprises a portable unit having a display screen and a data entry means for communicating and receiving information.

In an embodiment, the system further comprises an ECG (electrocardiogram) unit to monitor the heart rate of the person in the target zone.

In an embodiment, the system further comprises a plurality of sensors such as health sensor, pulse sensor, and temperature sensor to determine health conditions related to the person, where such determination is preferably conducted in real time.

In an embodiment, the system further comprises a smoke emission unit in connection with the microcontroller, which emits smoke upon detecting an incoming bullet to perturb the visibility of the person to the shooting enemy.

In an embodiment, the system further comprises an emergency button in connection with the microcontroller and the communication unit, which when pressed by the person transmits the location and health data of the person to a remote server.

In an embodiment, the system further comprises a data storage system in connection with the microcontroller to store information such as the health and whereabouts of the person, the effective bullet hits, location of the enemy, battle hot-spots, type of bullets used by the enemy.

The system further comprises a power supply in electrical connection with the electronic components of the system, which need power supply such as the microcontroller, the radar antennas, the feedback units and the sensors. The power supply can be through a battery or a solar power supply or charger.

The detection system can be installed in any apparel or garment that can be worn by the person such as a jacket or a vest to be placed on a body.

In another aspect, the present invention provides for a bullet detection system to be deployed over an object (other than a person), comprising an array of radar antennas deployable over the body of the object such as each radar antenna has a signal coverage covering a specific zone on the object for transmitting and receiving microwave detection signals for detecting incoming bullets, and a microcontroller in connection with the radar antennas for processing the detection signals received by the radar antennas and for determining incoming bullets in direction of the object before their arrival and the associated target location(s) on the object. The system further comprises a notification system for notifying a surveillance user of the incoming bullets and associated target location zones on the object.

In an embodiment, the detection system is connected to various other systems in the vehicle such as brakes, steering, accelerator, hydraulics, rotors, to automatically maneuver the speed and direction of the vehicle when an incoming bullet is detected in a specific target location zone thereby moving the vehicle away from the estimated bullet trajectory.

In an embodiment, the detection system further comprises shielding components mounted on different locations on the vehicle.

The system further comprises a plurality of smoke emission units deployed on the vehicle, which emit smoke in case of incoming bullets in order to perturb the visibility of the vehicle to the shooting enemy.

In an embodiment of the invention, the object is a vehicle such as a car, truck, battle tank, aircraft, jet, or a helicopter. In an embodiment, the detection system further comprises a navigation system in communication with the microcontroller for navigating the vehicle to dodge or move away from the incoming bullets or to provide any security means to avoid such incoming bullets. In an embodiment, the detection system further comprises shielding components in connection with the microcontroller for activating such shields to protect and shield against incoming bullets in the target location zones where the bullets are directed.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which—

DETAILED DESCRIPTION OF THE INVENTION

The aspects of the detection system according to the present invention will be described in conjunction with FIGS. 1-11. In the Detailed Description, reference is made to the accompanying figures, which form a part hereof, and in which is shown by way of illustration specific embodiments in which the invention may be practiced. It is to be understood that other embodiments may be utilized and logical changes may be made without departing from the scope of the present invention. The following detailed description, therefore, is not to be taken in a limiting sense, and the scope of the present invention is defined by the appended claims.

Figure 2A:
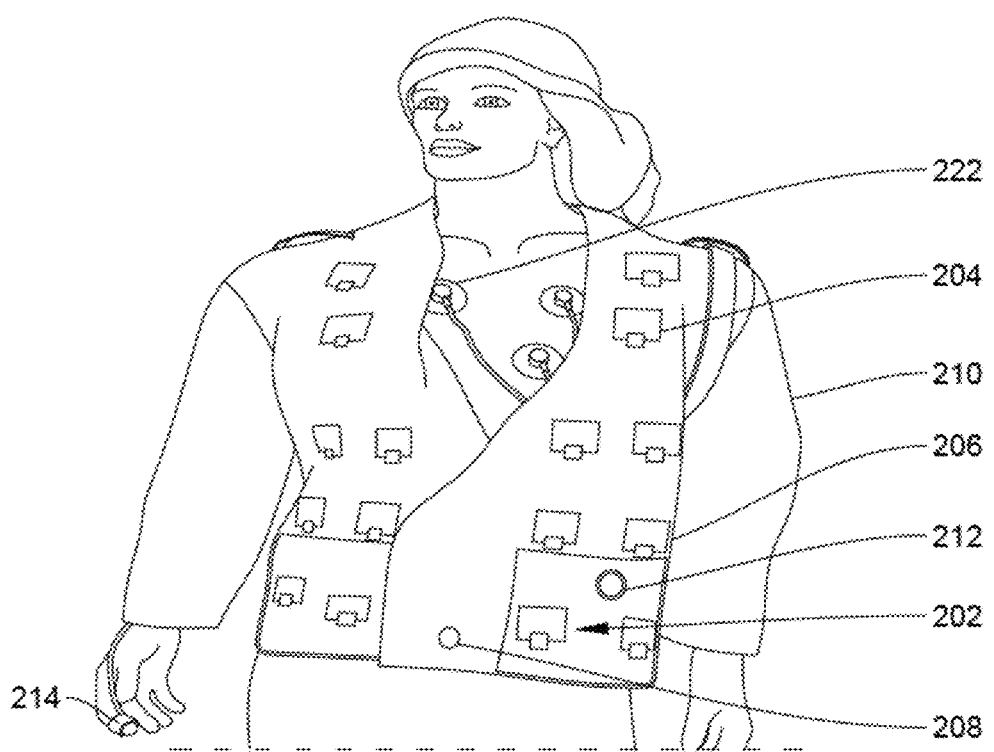
FIG. 2A and FIG. 2B illustrate a prototype of a jacket equipped with the detection system worn by a person showing the positioning of the various components of the detection system in accordance with an embodiment of the present invention.
Figure 2B:
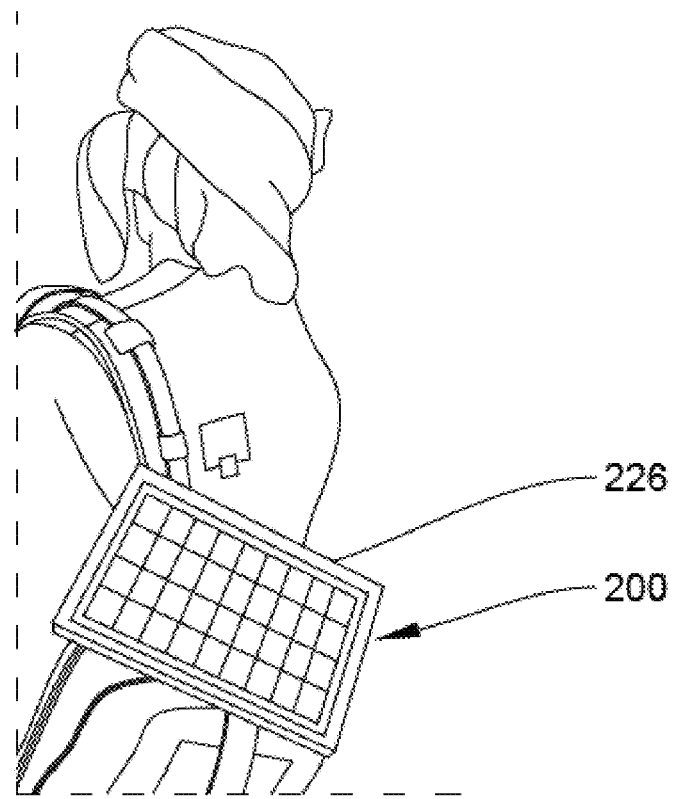
Figure 3:
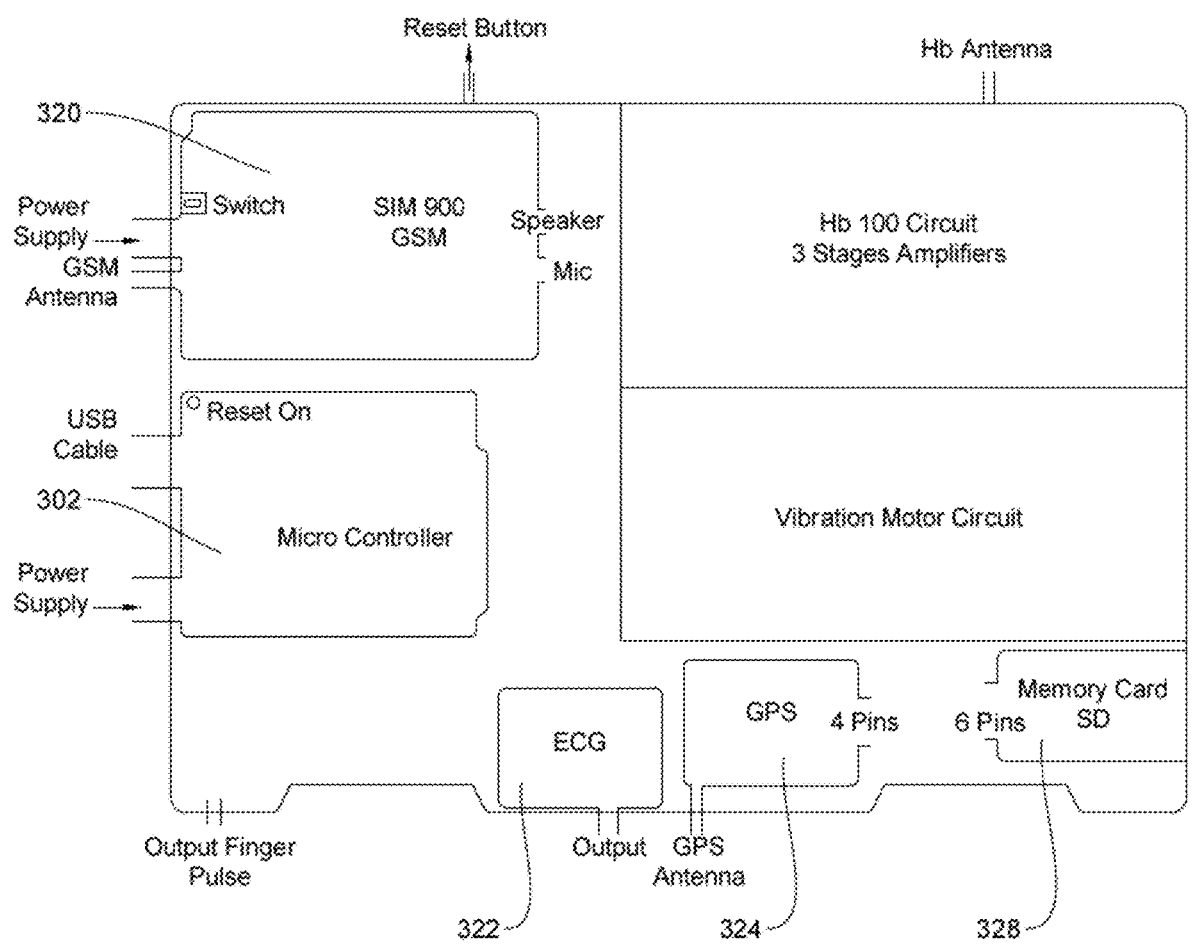
FIG. 3 illustrates a Printed Circuit Board (PCB) layout of the various components of the detection system in accordance with an embodiment of the present invention.

In an aspect of the invention, the present invention provides a bullet detection system 200 comprising a radar antenna 202, a feedback unit 208 and a microcontroller 302 as illustrated in FIGS. 2A, 2B and 3. The radar antenna 202 is preferably a micro-strip radar antenna which is configured to be deployed over the body of the person (or a specific part of the body such as the torso) either directly or indirectly by being embedded or placed on a piece of garment to be worn by the person such as a jacket or a vest. The radar antenna 202 is configured to cover in terms of signal coverage the part of the body to be protected against incoming bullets. The radar antenna 202 covers a specific zone of the body such as the detection by said antenna 202 of an incoming bullet is an indication of the specific zone of the body to which the bullet is being directed (the target location zone). The radar antenna 202 is being mapped to a corresponding feedback unit 208 positioned in proximity of the radar antenna 202. The radar antenna 202 and the corresponding feedback unit 208 are connected to the microcontroller 302 which receives the microwave signals detected by the radar antenna 202, processes these to determine any incoming bullets based on data processing analysis, determine the exact target location zone of the bullet on the person's body based on the data processing analysis as a function of the location of the radar antenna 202 having detected the arrival of such an incoming bullet, and triggers the feedback unit 208 corresponding to the radar antenna 202 for providing a sensation as an indication of an incoming bullet to that specific location on the person's body which would lead the person to dodge or move to avoid the incoming bullet.

In another aspect of the invention, the present invention provides a bullet detection system 200 comprising an array of radar antennas 202, 204 and 206, an array of feedback units (vibration units, electrical shock generators, sound generators) 208, 210 and 212 and a microcontroller 302 as illustrated in FIGS. 2A, 2B, 3. The array of radar antennas 202, 204 and 206 are preferably micro-strip radar antennas which are configured to be deployed over the body of the person (or a specific part of the body such as the torso) either directly or indirectly by being embedded or placed on a piece of garment to be worn by the person such as a jacket or a vest. The array of radar antennas 202, 204 and 206 are configured to cover in terms of signal coverage the different portions of the body (or part of the body) to be protected against incoming bullets. Each of the radar antennas 202, 204 and 206 cover a specific zone of the body such as the detection of the an incoming bullet by said radar antenna is an indication of the specific zone of the body to which the bullet is being directed (the target location zone). Each of the radar antennas 202, 204 and 206 are being mapped to a specific feedback units 208, 210 and 212 positioned in proximity of the radar antennas 202, 204 and 206 such that each radar antenna among the array of radar antennas 202, 204 and 206 has a corresponding feedback unit (at least one) among the array of feedback units 208, 210 and 212. The array of radar antennas 202, 204 and 206 and corresponding feedback units 208, 210 and 212 are connected to the microcontroller 302 which receives and transmits the microwave signals detected by the radar antennas 202, 204, 206, process these to determine any incoming bullets based on data processing analysis, determine the exact target location zone of the bullet on the person's body based on the data processing analysis as a function of the location of the radar antenna having detected the arrival of such an incoming bullet, thereby triggering the feedback unit corresponding to that specific radar antenna for providing a sensation as an indication of an incoming bullet to that specific location on the person's body which would lead the person to dodge or move to avoid the incoming bullet. The data processing analysis comprises comparing the frequency of the transmitted microwave signals to the received microwave signals for determining any change in frequency (higher frequency of a received signal with respect to a transmitted signal) which would be indicative of the detection of an incoming bullet. The radar antenna having received such a higher frequency signal would be the one positioned in the target location zone targeted by the bullet, and the feedback unit mapped to that specific radar antenna and positioned in proximity thereof will be triggered to vibrate. The array of radar antennas 202, 204 and 206 used are preferably in the microwave range.

The mechanism of the detection system 200 of the present invention is to mainly detect and alert the solider from the incoming bullet within a very long range, allowing the soldier to have a few valuable seconds to avoid the bullet, and save his life and at the same time prepare for a counter-attack. This mechanism of detection works by using the Doppler microwave radar. The wavelength of the bullet radar is within the V band, ranging from 40 GHz to 74 GHz with a wavelength range of 4 mm to 7.5 mm, which is sufficient to detect an incoming bullet. The starting maximum range that the radar can detect is from 2000 meters to 6000 meters. However, this detection zone is adjustable and is directly proportional to the power supply supporting detection system 200. The greater the power supply, the larger detection area. Additionally, for the detection system 200 to work efficiently the cross-section of the incoming bullet is 0.001 $m^2$ or more and the radar cross section (RCS) is −30 dB.

In an embodiment of the invention, the detection system 200 comprises many additional advantages such as exposing the rival/enemy location, showing the full health data of the injured soldier, recording the said data and transmitting the data to the base enabling medics to timely arrive at the location and provide required treatment. The importance of designing a system that detects microwave signals is mainly due to the reason that bullets are very fast and when released travel faster than the speed of sound depending on certain conditions such as type of the handgun, speed of the wind, air temperature, humidity and atmospheric pressure, and the type of bullets and guns. Hence, using a sound sensor to detect the bullets would not be sensible because it would not be as fast as a microwave signal. Moreover, microwave signals are widely used for point-to-point communications because of their small wavelength, which allows conveniently sized micro strip antennas to direct them in narrow beams, which can be pointed directly at the receiving antenna. A higher frequency radar will result in a smaller radar antenna size, making it more suitable to be deployed over a person's body or piece of garment such as a vest or jacket worn by a person. Once the bullet is released from the gun barrel the microwave radar transmits electromagnetic signals in the detection zone which will detect the incoming bullets by the receiving microwave signals having different frequencies that is caused by a motion in the surveillance zone according to the Doppler effect, wherein the frequency for an object that's moving towards the radar will have a higher frequency.

In an embodiment of the invention, the detection system 200 additionally comprises a clutter-filtering device, making the detection system 200 extremely accurate to detect only the bullet directed to a specific target location. Additionally, presence of the clutter filtering system increases the accuracy of detecting the trajectory of the incoming bullet, by eliminating undesirable noises released upon firing a bullet, which would otherwise interfere with the microwave signals.

As mentioned above the detection system of the present invention particularly comprises three main components, which are the array of radar antennas 202, 204 and 206 and feedback units 208, 210 and 212 for being deployed over a person's body, where the array of radar antennas 202, 204 and 206 and feedback units 208, 210 and 212 are in connection with a microcontroller 302.

The array of radar antennas 202, 204 and 206 receive the microwave signals that are released upon a bullet being fired from a gun barrel and these signals are then transmitted to the microcontroller 302. The microcontroller 302 processes these microwave signals to determine any incoming bullet and the specific target location zone and triggers the feedback unit positioned within that specific target location zone. The feedback units 208, 210 and 212 upon receiving this microwave signal provides a sensation on the exact part the body of the person that is targeted by the bullet. Because of this sensation experienced by the person, the person dodges or moves preventing himself/herself from being hit by the bullet.

The detection system 200 comprises an array of radar antennas 202, 204 and 206, which are placed at different parts on the person's body along with corresponding feedback units 208, 210 and 212, to efficiently detect the incoming signals and provide the required sensation.

The array of radar antennas 202, 204 and 206 and the corresponding feedback units 208, 210 and 212 are in close connection with the microcontroller 302, which process the signals and effectively transmits to the specific feedback unit to produce a sensation. Since the detection system 200 can efficiently detect surrounding threats, one of the key advantages of such a detection system 200 is that it will help the person to prevent and protect himself/herself from unexpected attacks resulting in building up their confidence and improving combat skills in the event of a battle.

The detection system 200 of the present invention can be mounted on or embedded within an apparel or piece of garment such as a vest or jacket worn by a person in the battlefield or for other civil defense purposes.

In an embodiment of the invention, the detection system 200 also comprises anti-radiation stickers, preferably placed around the body of the person beneath the antenna towards the backside, to absorb the radiation released from the electromagnetic waves, protecting the person on whom such a system is deployed, from the harmful effects of radiation. In addition, there will be a heat protection barrier between the radar and the body of the soldier to protect it from the heat of the used parts in the system (radar).

The detection system 200 of the invention is preferably made from various heat resistant materials including but not limited to Nomex or Aromatic Polyamide, which are nylon-like materials. These are highly resistant to the extreme or high temperatures, thereby protecting the person form the high heat generated by explosives.

In an embodiment of the invention, the detection system 200 also comprises health detectors comprising a plurality of sensors 214, 216, 218 for detecting health conditions of the person. These sensors preferably comprise a pulse monitor 214, a health sensor 216 and a temperature sensor 218. These sensors 214, 216, 218 are in connection with the microcontroller 302 for detecting the health condition of the person based on the readings of these sensors 214, 216, 218.

In an embodiment, the detection system 200 further comprises a communication unit 220 (such as a GSM unit) for notifying a remote unit such as a remote monitoring unit located at a military base of the health condition of the person. Preferably, said notification is conducted when the microcontroller 302 detects a bad health condition of the person, which can be due to an injury by a bullet for example. In an embodiment, the microcontroller 302 processes the readings of the health sensors 216 in conjunction with the readings of the antennas 202, 204 and 206 to determine a likelihood of whether the person has been hit by a bullet. Preferably, the notification by the communication unit 220 comprises notifying the remote unit of any such incidence based on the determination by the microcontroller 302.

In an embodiment, the detection system 200 further comprises bullet sensors to detect whether the person has be effectively hit by a bullet. Preferably, such bullet sensors comprise pressure sensors deployed over the person's body. Preferably, these bullet sensors are mapped to the array of radar antennas 202, 204 and 206 and to the feedback units 208, 210 and 212 to determine the accuracy between the proactive detection of incoming bullets to the target location zones and the location of the bullets, which have effectively hit the person. This can help improve the accuracy of the detection system 200 over time, and provide for a machine learning data, which can be self-improved over time based on these learnings and measurements.

The health detectors 214, 216 and 218 are placed in different locations on the person's body, thereby transmitting required information regarding the person's health to a remote monitoring unit at the base camp. The heath sensors 214, 216 and 218 preferably further comprise an ECG (electrocardiogram) unit 222, which constantly monitors the heart rate/respiratory rate of the person/soldier, displaying the number of beats per minute, and the pulse oximetry, which reads the amount of oxygen in the blood. In case of an abnormal health condition owing to injuries or other unfavorable situations, the ECG unit 222 sends an alert to a remote monitoring unit at the base camp, when it detects such abnormal health conditions and can send help to that person.

The temperature sensor 218 monitors heat injuries, heat illnesses and heat stress, which would occur when the soldier is exposed to extreme heat such as heatstroke, which is a medical emergency that can cause death if the treatment is not provided in time. In case of an abnormal rise or fall in body temperature, this temperature sensor 218 will transmit a signal to the remote monitoring unit at the base camp notifying them of the soldier's health. In addition to the detection system 200 being linked with a remote monitoring unit at the base, the detection system 200 is also linked to a smart watch worn by a person on whom the said system is deployed, enabling all health data received and sent from the detection system 200 to be available on the person's smart watch, enabling him/her to store the personal information and keep themselves updated of their health.

In an embodiment, the detection system 200 comprises a global positioning system (GPS) 224 which is connected with the microcontroller 302 and the communication unit 220. The GPS system 224 provides for the location of the person in the battlefield and updates the military camps with the geographical path of the soldier. In the event that the person was unable to save himself from the bullet and got injured as a result, this detection system 200 would still prove to be beneficial as the health sensors 216 keep continuously monitoring and in case of any abnormalities, the heath sensors 216 and the GPS system 224 which are connected to the communication unit 220 can send information about the soldier's condition and location to a remote monitoring unit at the base camp to be able to send the medical team to the injured soldier's location and provide for effective treatment.

In an embodiment, the detection system 200 further comprises an emergency button in connection with the microcontroller 302 and the communication unit 220. The emergency button serves as an effective attribute of the detection system 200, in the event that the soldier is unable to reach the military server due weak communication signals. The emergency button is connected with the communication unit 220 and when pressed by the person in a dangerous situation transmits a signal to the remote monitoring unit at the military base camp informing the military personnel at the base, the location of the user with their current health data, in case a person is injured and is in need of medical assistance. The emergency button further has additional features such as voice messaging and live camera streaming of the person's current location. The emergency button preferably comprises a microphone and a 360-degree camera installed within it to overcome precarious situations to bring help to the soldier efficiently.

In an embodiment, the detection system 200 of the invention comprises a mine detecting system, which can be placed in the shoe of a person or under a type of vehicle increasing productivity and providing extra support on a battlefield.

In an embodiment, the detection system 200 of the invention comprises a smoke emission unit that emits smoke in case of incoming bullets in order to perturb the visibility of the enemy shooting the bullets.

The detection system 200 is also collaborated with explosive killer drones. The killer drones are programmed in a way to to fly toward the enemy location and self-explode destroying enemy weapons or enemy soldiers in the process.

In another aspect, the present invention provides an interior first aid suit to be worn by the person, which is collaborated with the detection system 200. The suit comprises of small bags filled with Xstat positioned all over the person's body. Xstat is a homeostatic device for the control of severe, life-threatening bleeding. A rapidly expanding sponge will fill a gunshot wound immediately. As a result, this will prevent the loss of blood and consequently save lives until support arrives.

In an embodiment, the detection system 200 further comprises a power supply either in the form of a battery or a solar charger 226 (preferably solar panels) to continuously charge the system effectively during day and night time. The solar panels 226 provide a flexible method of charging as the solar panels 226 can serve as a secondary source of power supply to support the primary source of power supply, being the battery.

In addition to the above-mentioned components, the detection system also comprises a memory card 228 in connection with the microcontroller 302 (and as required with the other components of the device) to store data processing criteria used by the microcontroller 302 (such as benchmarking information), events related to the detection system such as incoming bullet detections, bullets avoided by the person, effective bullet hits, locations of the person during various conditions such as intensive shooting and fighting events, health conditions during the person's journey or during health drop periods, and other information about the soldier's health and whereabouts. This information can be sent by the communication unit to the remote unit to assess the battle circumstances in real time, or after the event such as determining hot battle spots and locations of the enemies and so on.

In an embodiment of the invention, the detection system 200 determines the location of the enemy based on the microwave signals received by the radar antennas. This is for example by determining the direct line sight of the bullet based on the signals received, the projection trajectory, the speed of the shot and the distance between the person and the source from where the bullet has been fired. The determination of the location of the enemy source can be determined based on the fluctuation of the signal frequency related to a specific bullet as a function of time. The determination can also be conducted using the take took between the detection of the incoming bullet and the time the bullet has reached in proximity of the person or has effectively hit the person. For this purpose, the detection system 200 preferably further comprises a timer or a clock to make such measurement. This information is preferably stored in the memory card 228 and/or sent to the remote unit using the communication unit.

In an embodiment of the invention, the detection system 200 analyses the type of bullet being fired and this is by measuring the cross section of the bullet using the received signals. The memory card 228 would store information with respect to the type of bullets and associated cross sections and the microcontroller 302 would make such determination by processing the received signals to determine the cross section of the incoming bullet and mapping this to the stored information for determine a type of bullet or weapon used. This information is preferably stored in the memory card 228 and/or sent to the remote unit using the communication unit 220. Due to the importance of data that the detection system 200 shares or sends/receives from/to the remote monitoring unit at the military base, it is imperative that the system comprise of anti jammers to secure data shared from being stolen by the enemy.

In an aspect of the invention, the detection system in accordance with the various embodiments of the present invention can be used in connection with subjects or objects other than a person, such as vehicles and/or buildings in making the required adaptations.

The system 200 of the present invention has the adaptability to be applied to range of personnel including but not limited to army soldiers, police officers, politicians, clerics, entrepreneurs, businessperson, highly ranked individuals, diplomats, astronauts, all of whom may require excessive protection in different scenarios. These individuals can protect themselves from snipers or shooters during public speaking, as the detection system 200 deployed on the person's body will enable him/her to dodge an incoming bullet based on the above mentioned mechanism and save his/her life.

Further, since the detection system 200 of the present invention can also locate enemy hideouts based on the signals received by the antennas in the system deployed on the person's body. This will further ease the arrest process as the location of the enemy can be identified in addition to the bullet identification. Additionally, In an aspect of the invention, the detection system 200 is configured to be mounted and deployed on a robot. Applying this system to robots can improve the reliability and responses made during wars with intelligent robots with faster stimuli, decreasing human casualties.

FIG. 3. Depicts a PCB layout comprising a microcontroller 320, a GSM unit 320, ECG unit 322, a GPS unit 324 and a memory card unit 328 in connection with each other.

Figure 4A:
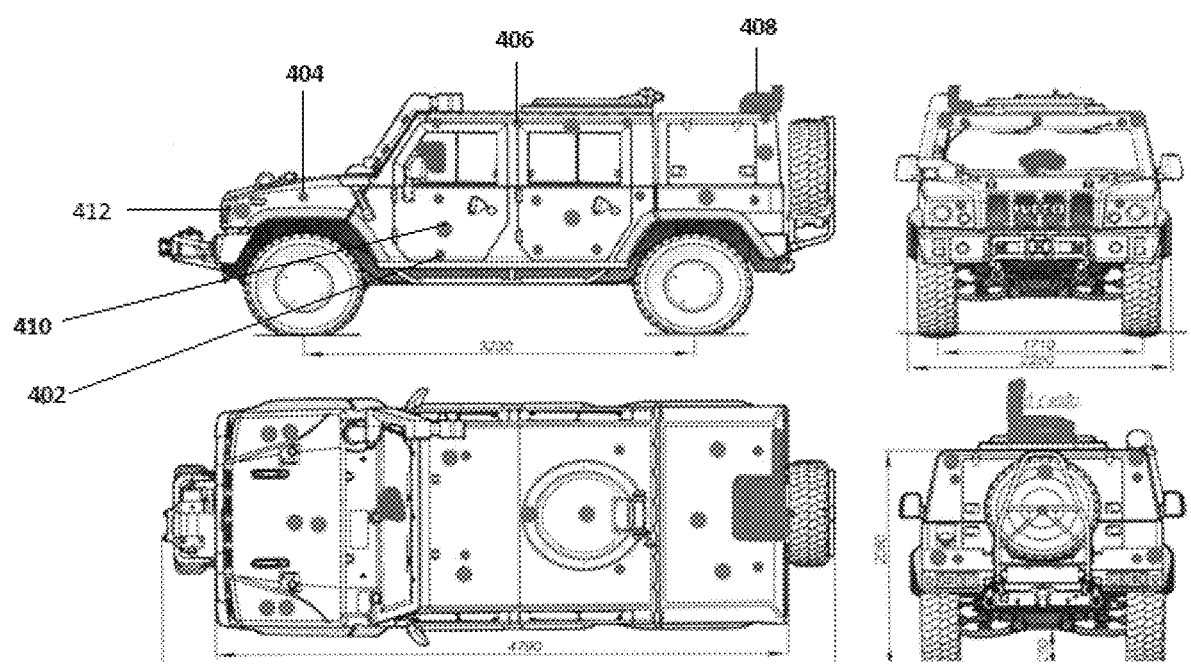
FIG. 4A and FIG. 4B illustrate a vehicle equipped with the detection system in accordance with an embodiment of the present invention.
Figure 4B:
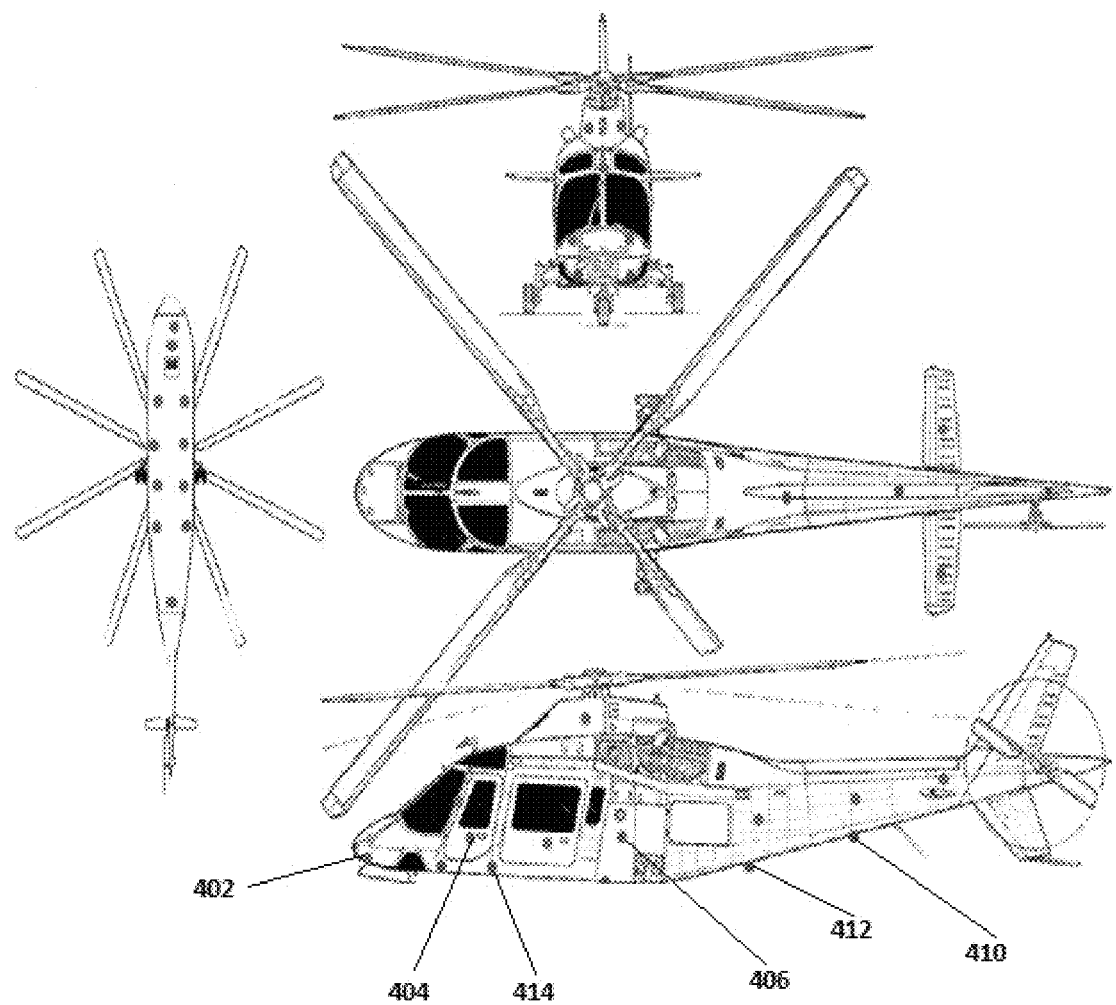

In an aspect of the invention, the bullet detection system is configured to be mounted and used in connection with a vehicle including but not limited to cars, trucks, battle tanks, aircrafts, helicopters, fighter planes, jet planes, satellites, spaceships, naval or military ship as illustrated in FIGS. 4A and 4B.

For such an application, the detection system 400 to be deployed on a vehicle comprises array of radar antennas 402, 404, 406 are deployed in different locations of the vehicle such as each radar antenna covers in terms of signals a specific zone of the vehicle. The detection system 400 further comprises a notification unit in connection with the microcontroller to notify a vehicle operator of the incoming bullets.

In an embodiment, the detection system 400 is connected to a navigation system 408 of the vehicle through the microcontroller for navigating the vehicle away from the incoming bullets. Preferably, the detection system is connected through the microcontroller with the various car systems, such as brake, steering, accelerator, hydraulics, rotors etc. to automatically maneuver the speed and direction of the vehicle when an incoming bullet is detected in a specific target location zone thereby moving the vehicle away from the estimated bullet trajectory saving the personnel inside the vehicle. Preferably, the detection system 400 is connected through the microcontroller to shielding components for shielding the vehicle, in the specific target zone locations, of any incoming bullets. For example, a shielding component can be mounted on the windows and are activated to shield the windows corresponding to the target location zones associated with the incoming bullets.

In an embodiment, the detection system 400 comprises, in addition or instead have, display sensors (such as led lights) inside the vehicle for displaying the locations targeted by the incoming bullets. Each display sensor inside the vehicle is preferably associated to a specific antenna outside the vehicle and positioned in the same location from the inside. In an embodiment, the detection system 400 comprises a plurality of smoke emission units 410 412, 414 which emits smoke in case of incoming bullets in order to perturb the visibility of the vehicle to the shooting enemy. In an embodiment, the detection system 400 in through the microcontrollers is in connection with the missiles, rifles, and/or machine guns deployed on the vehicle, enabling to automatically fire away on receiving a signal from the antenna, when an incoming bullet is detected in a specific target zone of the vehicle.

In another aspect of the invention, the detection system is configured to be mounted on buildings in different locations of the building such as each antenna covers in terms of signals a specific zone of the building. In an embodiment, the detection system is connected through the microcontroller with an alarm system, which automatically triggers off, when an incoming bullet is detected in a specific target location zone thereby alerting the persons inside the building to evacuate. More preferably the detection system 400 can be connected to a dual alarm system. In an embodiment, the detection system is connected through the microcontroller to shielding components for shielding the building, in the specific target zone locations, of any incoming bullets. For example, a shielding component can be mounted on the windows and/or glass panes, which are activated to effectively shield the windows corresponding to the target location zones associated with the incoming bullets.

In an embodiment of the invention, the detection system can also be used in various other situations for detecting meteoroids in outer space, which can negatively impact spacecrafts, astronauts, satellites, and space projects. Collisions with meteoroids cause serious damage or failure to a spacecraft, and maybe life threating to astronauts. The detection system can be configured to be used to determine the trajectory of the incoming meteoroid based on the incoming signals received by the antenna, and effectively notify the astronaut or the spaceship of the imminent threat.

In another embodiment of the invention, the detection system can also be used to identify other objects, birds and/or small animals that would otherwise hinder the motion of a vehicle. Bird strikes or birds coming in way of flights can account for a lot of expenses due to engine maintenance and flight cancellations. The detection system of the present invention enables in detecting birds or other objects hindering the motion of the vehicle and void disruptions.

The detection system of the present invention is to effectively prevent a person from being shot on and save his/her life. In addition to this, the detection system of the present invention is also able to locate the direction of the incoming bullet based on its trajectory and thereby expose the enemy location with accurate coordinates using characteristics of the radar with horizontal and longitudinal dimensions include azimuth angle, elevation angle and projection trajectory, which measure the speed of the shot and distance between the radar and the target. The detection system can also identify the type of bullet used by the enemy using arithmetic equations to determine the surface area of the cross-sectional area, the velocity. Since the detection, system is coupled to a memory card via the microcontroller to send and store benchmarking information to a remote monitoring unit at the base. This will enable the personnel at the base to check the specifications of the bullet, identify these bullets on the database, and thereafter assess the strength of the enemy.

Figure 1:
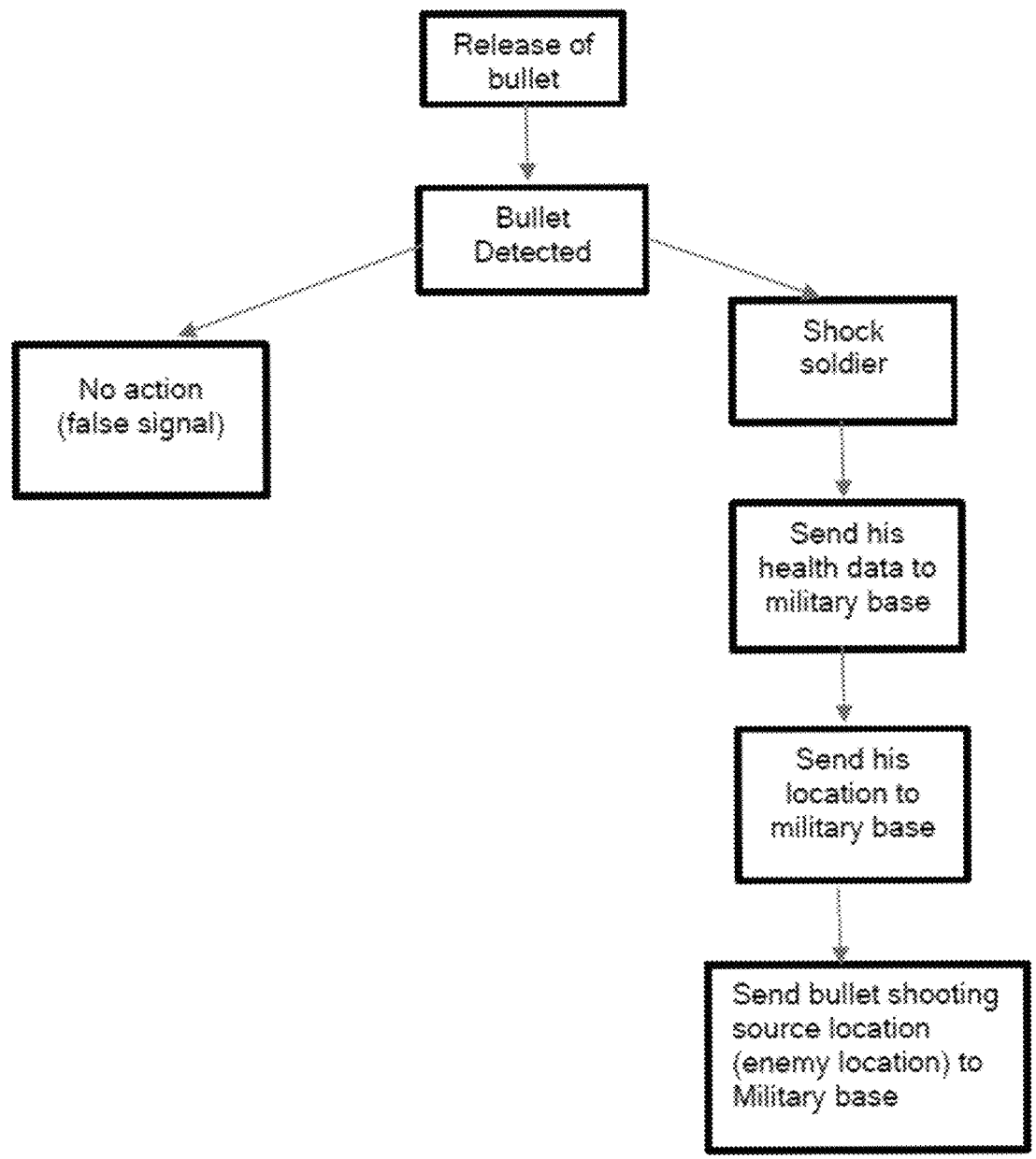
FIG. 1 illustrates a flow chart describing the mechanism in which the bullet is detected by the system and information is transmitted to a remote server at a military base in accordance with an object of the present invention.

As mentioned above, the presence of a plurality of sensors in the detection system in connection with the microcontroller and the communication unit also the physiological health data of a person, which directly provides information to the remote monitoring unit at base regarding the personnel's health condition, specifically in combat situations or in case of abnormal health conditions. In addition to the above mentioned advantages, the detection system is also able to identify the source and type of weapon from which the bullet is released, by analyzing the speed and cross section of the bullet enabling the person to know and understand the weapons used by the enemies in the battlefield, thereby preparing them in understanding the defense systems used by the rivals FIG. 1 illustrates a flow chart describing the mechanism in which the bullet is detected by the system and information is transmitted to a remote monitoring unit at a military base in accordance with an object of the present invention.

As mentioned above, the detection system of the present invention is also able to locate the direction of the incoming bullet based on its trajectory and thereby expose the enemy location with accurate coordinates using characteristics of the radar with horizontal and longitudinal dimensions include azimuth angle, elevation angle and projection trajectory, which measure the speed of the shot and distance between the radar and the target. The detection system can also identify the type of bullet used by the enemy using arithmetic equations to determine the surface area of the cross-sectional area, the velocity.

In an embodiment of the invention, the slant range formula applied to the detection system in accordance with an embodiment of the present invention is as follows:

$$R = \frac{c0.t}{2} \qquad \text{(Equation 1)}$$

Where, $c0$=speed of light=$3.10^8$ m/s, t=measured running time [s] and R=slant range antenna—aim [m]. The distance are expressed in kilometres or nautical miles (1 NM=1.852 km). In the present invention 'Range' is defined as the distance from the radar to the target along the line of sight. If time (t) is known, the distance (R) can be calculated based on the below mentioned equations, $$V = \frac{s}{t} \qquad \text{(Equation 2)}$$

$$c0 = \frac{2.R}{t} \qquad \text{(Equation 3)}$$

The factor of two in the equation comes from the observation that the detection system pulse might travel to the target and back before detection, or twice the range.

$$R = \frac{c0.t}{2} \text{ in metres} \qquad \text{(Equation 4)}$$

where $c_0=3.10^8$ m/s, is the speed of light at which all electromagnetic waves proagate.

The above equations to determine the unambigiuos range. Pulse-repetition frequency (PRF) determines the maximum unambigiuos range of a given radar before ambiguities start to occur. The pulse width (Pw) indicates complete echo impulse must be received. If the transmitted pulse is very short (one microsecond) it can be ignored. If the pulse is very long like (up to 800 microseconds) the backscattered signal must be compressed in the receiver, it must be received in full length therefore. The Pulse reputition time (PRT) is important when determining the maximum range because target return-times that exceeds the PRT of the detection system appears at incorrect locations (ranges) on the radar screen. Returns that appear at these incorrect ranges are referred to as ambiguous returns, second-sweep echoes or second time around echos.

$$R_{max} = \frac{c0.(PRT - Pw)}{2} \quad \text{(Equation 5)}$$

$$R_{max} \approx \frac{(PRT - Pw)\text{in}[\mu s]}{6.66 \; \mu s} \text{in [km]} \quad \text{(Equation 6)}$$

where $c_0$ is the speed of light with $3.10^8$ m/s

Track initiation is the process of creatin a new radar track from unassociated radar plots. Track maintenance is the process in which a decision is made about whether to end the life of a track. If a track was not associated with a plot during the plot to track association phase, then there is a chance that the target may no longer exist.

Track Smoothing: The role of the track-smoothing function is to take the current known state (i.e. position, heading, speed and possibly acceleration) of the target and predict the new state of the target at the time of the most recent radar measurement.

Antenna gain:

$$G = \frac{4.\pi.A.Ka}{\lambda^2} \quad \text{(Equation 7)}$$

Antenna area:

$$P_e = \frac{Ps.G^2.\sigma.\lambda^2}{(4.\pi)^3.R^4} \quad \text{(Equation 8)}$$

Solving for range:

$$R = \sqrt[4]{\frac{Ps.G^2.\lambda^2.\sigma}{P_E.(4\pi)^3}} \quad \text{(Equation 9)}$$

For the detection system to detect targets at low heights, a reflection at the Earth's surface is necessary for which the following equation can be used:

$$R = Ka \sqrt[4]{\frac{P_s.G^2.\lambda^2.A_{z.t_i}}{K.T_0.n_R(4\pi)^3.d}} \cdot \sin\left(\frac{2\pi.h_m}{\lambda}\sin\gamma\right) \cdot e^{-0.115\delta_R.R_e} \quad \text{(Equation 10)}$$

where Ka=loss factor in place of Lges, ti=pulse length, T0=absolute temperature in K, d=clarity factor of the display terminal, δR=break-even factor, Az=effective reflection surface in place of σ, K=Boltzman's constant, nR=noise figure of the receiver, γ=reflected beam angle, Re=distance of the absorbing medium.

The azimuth resolution, R:

$$R_a = \frac{H.\lambda}{L.\cos\theta} \quad \text{(Equation 11)}$$

where H=height of the antenna, (height of the aeroplane), L=geometric length of the antenna, λ=wavelength of the transmitted pulses and θ=incidence angle In an embodiment of the invention, the detection system of the present invention is light, portable and could be easily placed on the soldier's body as a vest, cheap to produce, faster operation and highly efficient.

In an embodiment of the invention, the invention utilizes a new high technology portable defense system jacket that works by Doppler microwave radar that saves soldiers' lives in battlefield, and has many features such as alerting soldier from surrounding threats such as incoming bullet to the soldier's position, expose enemy location, and show the full health data and injured soldier location to the military camp.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims, which follow.

The invention claimed is:

1. A detection system comprising:
   an array of radar antennas and an array of feedback units, wherein each radar antenna within the array of radar antennas corresponds to a single feedback unit within the array of feedback units, and the array of radar antennas and the array of feedback units are configured to be deployed on a person's body; and
   a microcontroller in communication with the array of radar antennas and the array of feedback units, wherein the microcontroller is configured to receive microwave signals from the array of radar antennas, and is configured to process the received microwave signals to detect an incoming bullet and the associated target location zone on the person's body where the bullet is directed, and wherein the microcontroller is configured to activate a specific feedback unit of the array of feedback units positioned in the target location zone.

2. The detection system as claimed in claim 1, wherein the radar antennas are mapped to and positioned in proximity of the feedback units, and each radar antenna has a corresponding feedback unit mapped thereto and positioned in proximity thereof.

3. The detection system as claimed in claim 1, wherein the radar antennas detect the microwave signals upon release of a bullet from a gun barrel.

4. The detection system as claimed in claim 1, wherein the microcontroller triggers a feedback unit to provide a sensation upon detection of an incoming bullet in the target location zone in which the feedback unit is located on a specific part of the body.

5. The feedback unit as claimed in claim 1, wherein the feedback unit comprises at least one of a vibration unit, a sound generator, an electrical shock generator and a display sensor.

6. The detection system as claimed in claim 1, wherein the system further comprises a communication unit and a global positioning system to detect the location of the person and for transmitting said location to a remote monitoring unit.

7. The detection system as claimed in claim 6, wherein the remote monitoring unit comprises a portable unit comprising a use interface for communicating and receiving information.

8. The detection system as claimed in claim 1, wherein the system further comprises a plurality of health sensors comprising at least one of a pulse sensor and a temperature sensor for monitoring the health conditions of the person.

9. The detection system as claimed in claim 8, wherein the health sensor further comprises an electrocardiogram unit to monitor the heart rate of the person.

10. The detection system as claimed in claim 1, wherein the system further comprises a smoke emission unit in connection with the microcontroller, for emitting smoke upon detecting an incoming bullet to perturb visibility of the person to a shooting enemy.

11. The detection system as claimed in claim 1, wherein the system further comprises a data storage system in connection with the microcontroller to receive and record information comprising physiological activity of the person, a location of the person, effective bullet hits, a location of the enemy, battle hot-spot and a bullet type used by the enemy.

12. The detection system as claimed in claim 1, wherein the system further comprises a power supply.

13. The detection system as claimed in claim 12, wherein the power supply is a battery or a solar charger.

14. The detection system as claimed in claim 1, wherein the system is portable and mountable in any apparel or piece of garment such as a jacket or a vest.

15. A detection system, comprising:
an array of radar antennas;
a microcontroller configured to be deployed on a vehicle, wherein the microcontroller is configured to process microwave signals received from the array of radar antennas to determine arrival of a bullet and the associated target location zone on the vehicle; and
an array of display lights mapped to the radar antennas and configured to be positioned in proximity of the radar antennas for alerting an operator of the vehicle of incoming bullets.

16. The detection system of claim 15, wherein the system further comprises a navigation system in connection with the microcontroller for navigating the vehicle to avoid the incoming bullets.

17. The detection system as claimed in claim 15, wherein the system is connected via the microcontroller to various other systems in the vehicle comprising at least one of a brake, a steering, an accelerator, hydraulics, and rotors, to automatically maneuver speed and direction of the vehicle when an incoming bullet is detected in a specific target location zone thereby moving the vehicle away from an estimated bullet trajectory.

18. The detection system as claimed in claim 15, wherein the system further comprises a shielding component in connection with the microcontroller for activating a shield to protect and shield against an incoming bullet in the target location zone where the bullet is directed.

19. The detection system as claimed in claim 15, wherein the system further comprises a plurality of smoke emission units in connection with the microcontroller, for emitting smoke in case of incoming bullets to perturb visibility of the vehicle to a shooting enemy.

20. The detection system as claimed in claim 15, wherein the vehicle is a car, a truck, a battle tank, an aircraft, a helicopter, a fighter plane, a jet plane, a spaceship, a naval ship or a military ship.

* * * * *